US009492061B2

(12) United States Patent
Abraham-Fuchs et al.

(10) Patent No.: US 9,492,061 B2
(45) Date of Patent: Nov. 15, 2016

(54) ENDOSCOPY SYSTEM

(75) Inventors: Klaus Abraham-Fuchs, Erlangen (DE);
Rainer Graumann, Höchstadt (DE);
Rainer Kuth, Höchstadt (DE);
Johannes Reinschke, Nuremberg (DE);
Rudolf Röckelein, Erlangen (DE);
Sebastian Schmidt, Weisendorf (DE)

(73) Assignee: Siemens Aktiengesellschaft, Munich (DE)

( * ) Notice: Subject to any disclaimer, the term of this patent is extended or adjusted under 35 U.S.C. 154(b) by 2247 days.

(21) Appl. No.: 11/995,409

(22) PCT Filed: Jul. 10, 2006

(86) PCT No.: PCT/EP2006/064066
§ 371 (c)(1),
(2), (4) Date: May 27, 2008

(87) PCT Pub. No.: WO2007/023025
PCT Pub. Date: Mar. 1, 2007

(65) Prior Publication Data
US 2008/0249359 A1 Oct. 9, 2008

(30) Foreign Application Priority Data
Jul. 11, 2005 (DE) .......................... 10 2005 032 289

(51) Int. Cl.
| A61B 1/04 | (2006.01) |
| H01F 7/00 | (2006.01) |
| A61B 1/00 | (2006.01) |
| A61B 5/07 | (2006.01) |
| A61B 5/00 | (2006.01) |

(52) U.S. Cl.
CPC ....... *A61B 1/00147* (2013.01); *A61B 1/00158* (2013.01); *A61B 1/041* (2013.01); *A61B 5/073* (2013.01); *A61B 5/704* (2013.01); *A61B 34/70* (2016.02); *A61B 34/73* (2016.02); *A61B 2034/732* (2016.02)

(58) Field of Classification Search
USPC ................. 600/114, 117–118, 424; 128/899; 335/219; 5/681
See application file for complete search history.

(56) References Cited

U.S. PATENT DOCUMENTS

| 5,012,821 | A | * | 5/1991 | Tarver ........................... 128/876 |
| 5,590,429 | A |   | 1/1997 | Boomgaarden et al. |
| RE36,162 | E | * | 3/1999 | Bisek et al. .................. 378/146 |
| 6,076,527 | A | * | 6/2000 | Rottinghaus et al. ........ 128/869 |
| 6,709,387 | B1 | * | 3/2004 | Glukhovsky et al. ......... 600/109 |
| 2001/0012914 | A1 | * | 8/2001 | Kuth et al. .................... 600/415 |

(Continued)

FOREIGN PATENT DOCUMENTS

| DE | 43 13 843 | 11/1994 |
| WO | WO 2005/122866 | 12/2005 |

Primary Examiner — John P Leubecker
Assistant Examiner — Arnaldo Torres Diaz
(74) Attorney, Agent, or Firm — Schiff Hardin LLP

(57) ABSTRACT

An endoscopy system has an endo-robot that is navigable within an anatomical lumen of a patient by interacting with a magnetic field generated by an extracorporeal magnet system. The patient lies on a patient bed that is movable in one or more directions and/or orientations, and an obstacle detects objects in the movement path of the endo-robot in the anatomical lumen and produces a signal that causes the position and/or orientation of the patient bed to be altered dependent thereon.

12 Claims, 2 Drawing Sheets

(56) References Cited

U.S. PATENT DOCUMENTS

| | | |
|---|---|---|
| 2002/0198439 A1 | 12/2002 | Mizuno |
| 2003/0060702 A1 | 3/2003 | Kuth et al. |
| 2003/0184297 A1* | 10/2003 | Jakab .................... 324/318 |
| 2004/0181127 A1* | 9/2004 | Matsumoto et al. ......... 600/101 |
| 2004/0225188 A1 | 11/2004 | Kleen et al. |
| 2005/0059879 A1* | 3/2005 | Sutherland et al. .......... 600/411 |
| 2006/0004255 A1* | 1/2006 | Iddan et al. .................. 600/160 |

* cited by examiner

Stepper Motor

Retention Device

US 9,492,061 B2

ENDOSCOPY SYSTEM

BACKGROUND OF THE INVENTION

1. Field of the Invention

The invention concerns an endoscopy system.

2. Description of the Prior Art

In the implementation of methods in conventional endoscopy and in capsule endoscopy it may occur that, due to the position of the patient, intestinal loops lie in an intestinal section such that obstacles arise that cannot be surmounted or can be surmounted only with great difficulty by the endoscope or by the endoscopy capsule. Among such obstacles are, for example, kinks of the intestine, very narrow curves or the compression of intestine portions caused by organs (for example other intestinal loops) pressing thereupon.

Furthermore, given a recumbent position of the patient an intestine section can extend in the vertical direction. This position of the intestine section represents a "gravitational blockage" both for a conventional endoscope and for an endoscopy capsule since, in addition to the friction resistance of the endoscope or the endoscopy capsule in the intestine, the weight of the endoscope or of the endoscopy capsule must be overcome.

The aforementioned problems occur particularly in endoscopy with magnetically navigable endoscopy capsules (endo-robots) wherein only slight forces are exerted on the endoscopy capsule by an externally generated magnetic field.

A system for endoscopic observation of the body is known from DE 4313843 A1. This system has a coil device for generation of two homogeneous magnetic fields standing at an angle to one another and an endoscopic magnetic capsule on which a force is exerted due to the external magnetic fields. In order to enable locomotion of the endoscopic probe in the body due to the homogeneous magnetic fields, a relative movement of body and probe is needed. The movement of the body is achieved by a patient bed that can be shifted in the height, length and transverse directions and can be displaced around its longitudinal axis. The magnet system itself can additionally be moved relative to the body. The measures described here are intended to obtain a force acting on the endoscopy probe and thus to achieve a linear locomotion.

An endoscopy system in which a magnetic endoscopy capsule can be navigated in a hollow organ of a patient is described in US 2004/0181127. For this purpose, a magnetic field is generated by an external magnet system only at a point fixed relative to the magnet system. The movement of the endo-robot ensues exclusively via displacement and tilting of the patient bed. The navigation of the endo-robot is thus not always possible with the desired or required precision.

An endo-robot (magnetically navigable endoscopy capsule) with which minimally-invasive diagnoses and procedures can be implemented inside the body of a patient is known via DE 101 42 253 C1. The endo-robot has a bearing head in which measurement instruments and/or sample extraction and/or treatment instruments are integrated. The endo-robot furthermore has a linear magnet that is arranged collinear with the longitudinal axis of the endo-robot. The endo-robot is navigable via remote control by a magnet system acquiring the examination region of the patient, which magnet system generates a 3D gradient field.

A wireless endoscopy apparatus in the form of a swallowable capsule is disclosed in DE 103 17 368 B4, which capsule likewise has a permanent magnet that is installed along an established longitudinal axis. The endoscopy apparatus can be aligned from the outside via an externally applied magnetic field. The locomotion of the capsule through the digestive tract ensues via the peristaltic movements of the stomach-intestine musculature. A dye stored in a dye reservoir can be introduced in the tissue of the digestive tract via an outlet aperture connected with the ink reservoir.

A device for examination of a contrast agent progression in the body of a patient due to gravitation is known from DE 100 03 726 A1. The device includes an MR scanner with a patient positioning system that enables an angled positioning of the patient.

The prior art devices rely on the assumption that locomotion (possibly supported by a magnetic field) of an endoscopy capsule in the body is possible without further measures. Problems of the aforementioned prior art (namely to react to obstacles, curves, incidental organ positions) are not addressed. No information is provided regarding how these problems would be solved (automatically, if possible).

SUMMARY OF THE INVENTION

An object of the present invention is to provide an endoscopy system that enables an improved and possibly automated locomotion of an endoscopy capsule, in particular in problematic zones, and thus exhibits an improved precision in the navigation of the endo-robot.

The object is inventively achieved by an endoscopy system. Advantageous embodiments of the invention are the respective subject matter of further claims.

The endoscopy system having an external magnet system and at least one endo-robot as well as a patient positioning system, wherein at least one endo-robot is navigable in a hollow human or animal organ by a temporally variable and spatially inhomogeneous magnetic field generated by the external magnet system, and the patient positioning system has a patient bed that can be rotated around its longitudinal axis and/or can be inclined in its longitudinal axis and/or can be displaced in at least one spatial direction.

As used herein "endo-robot" means a magnetic endoscopy capsule (that is also designated as a magnetic capsule endoscope).

An endo-robot can be navigated in a hollow human or animal organ significantly more precisely by remote control not only by a magnetic field generated by the external magnet system at a point fixed relative to the magnet system, but also by a temporally variable and spatially inhomogeneous magnetic field that is generated in a working volume by the external magnet system such that a desired force and/or a desired torque acts on the endo-robot.

The working volume exhibits, for example, a diameter of 35 cm and a length of 20 cm. In order to be able to navigate the endo-robot from the stomach to the anus, the patient bed must be displaceable along its longitudinal axis.

The endoscopy system according to the invention includes a detector for detection obstacles to the movement of the endo-robot from which control variables for the position alteration of the patient positioning system can be derived in order, for example, to adjust the gravitational force (which acts both on organs or tissue parts and on the endo-capsule itself) so as to contribute to the removal of hindrances to the endo-capsule or to support the movement respective to the movement direction change of the endo-capsule. For example, by the rotation of the patient bed into a lateral position the patient is brought from his recumbent position into a lateral position. A horizontal movement is therewith achievable from a vertical movement of the endo-robot. When the vertical movement direction contains a movement of the endoscopy-capsule from below to above, then a horizontal movement is now possible in a comparably better manner. A necessary horizontal movement can be converted into a vertical movement from above to below by rotation of the patient bed.

Constrictions/contractions in the hollow organ due to other tissue parts or organs can also be remedied or at least minimized via the rotation or inclination adjustment of the patient bed, for example. Possible disadvantageous positions of the hollow organ itself (for example kinks) can also be moderated. In all cases described in the preceding the external magnet system is thereby "unburdened". The magnetic fields to be generated can possibly be reduced or are henceforth sufficient at a determined strength to realize a movement of the endo-capsule.

According to an advantageous embodiment of the inventive endoscopy system, the magnetic system can be rotated around its longitudinal axis and/or can be inclined in its longitudinal axis and/or can be displaced in at least one spatial direction. The patient bed of the patient positioning system and the external magnet system are therewith alternately displaced either alone (i.e. relative to the external magnet system) or together with this magnet system. In the latter case tilting of the patient bed and magnet system on an axis transverse to its longitudinal axis is also conceivable. Positions of the magnet system relative to the planned movement direction and/or the current position of the endo-capsule (position of the magnet in the capsule) can likewise be found in this manner, which positions ensure a maximum force introduction to the endo-capsule given simultaneous minimization of the magnetic field to be generated.

In an embodiment the endo-robot has a sensor device is provided for detection of obstacles, the sensor device detecting at least one counterforce that acts on it in the hollow organ. Such a sensor device could, for example, be based on one or advantageously a number of peripheral pressure sensors. The data transmitted from these sensors provide indications or specifications (possibly via further interposed software-supported evaluations) to the physician implementing the endoscopic examination) of how a manual displacement of the patient bed and/or of the magnet system should advantageously ensue.

In a further preferred development of the invention imaging methods are used as a means for detection of obstacles. Conclusions about obstacles of any type likewise can be made using such imaging methods, and instructions or specifications for displacement of patient bed and/or magnet system can be provided to the physician in essentially a semi-automatic manner.

In a particularly preferred embodiment the patient bed and/or the magnet system can be automatically moved via the control variables such that an optimal (i.e. as obstacle-free as possible) movement of the endo-robot through the lumen ensues and thus the power consumption of the magnetic coil system of the endo-robot is minimized and/or does not exceed a predeterminable maximum value. In this manner the treating physician can concentrate on the procedure itself since an optimal support of the movement of the endo-robot is automatically taken care of.

According to a further embodiment the endoscopy system has a patient bed that comprises at least in part a largely non-ferromagnetic material. It is therewith ensured that the temporally variable and spatially inhomogeneous magnetic field generated by the external magnet system is not adulterated.

In an advantageous manner the patient bed has at least in part a material with a low electrical conductivity. It is therewith reliably avoided that eddy currents are induced, in particular given rapid changes of the magnetic field.

DESCRIPTION OF THE PREFERRED EMBODIMENTS

Figure 1:
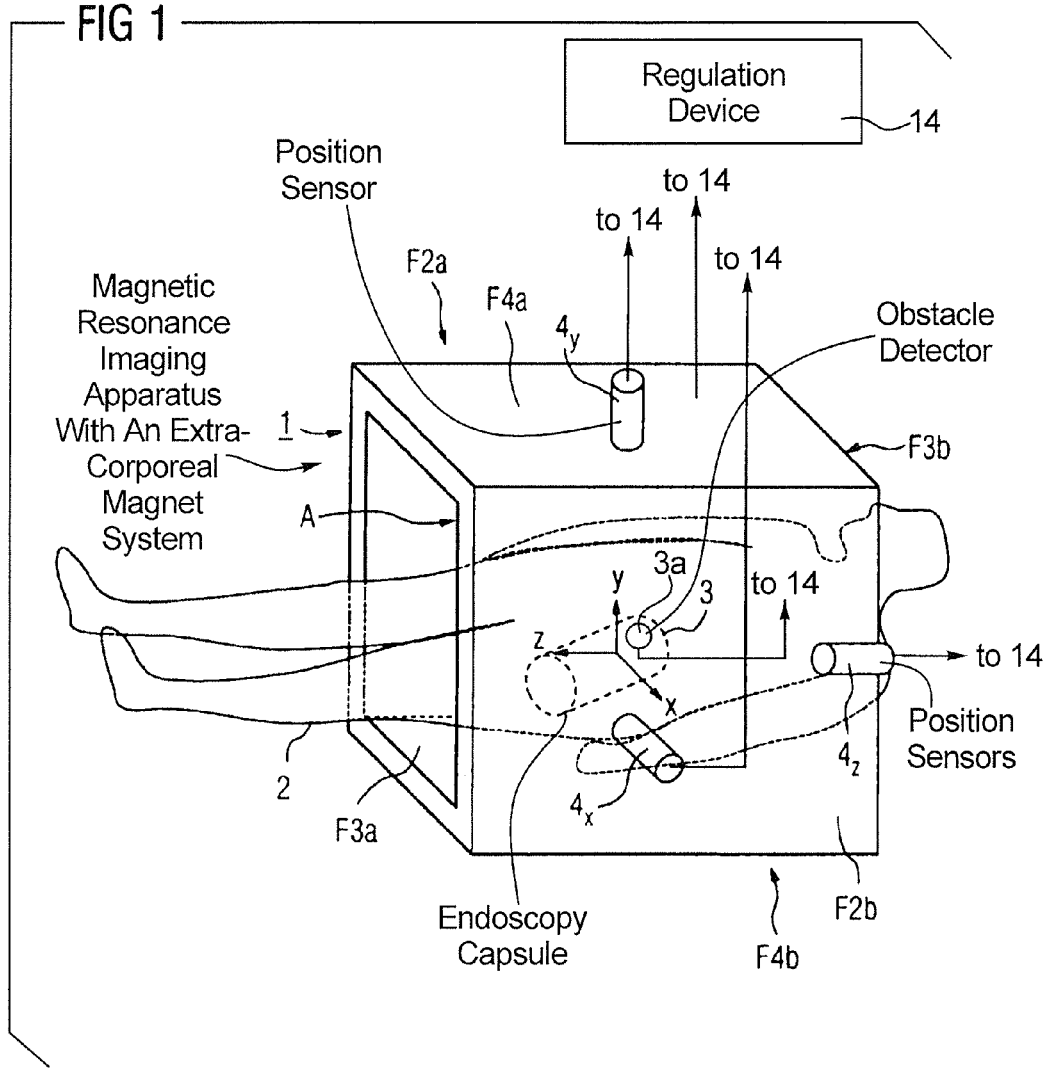
FIG. 1 illustrates an external magnet system for generation of a magnetic field.

In FIG. 1 a known (therefore not described in detail) magnetic coil system that is a component of an external magnet system is designated with 1.

The magnetic coil system 1 in the shown exemplary embodiment exhibits an approximately cubical external contour and is, for example, a magnetic coil system of a magnetic resonance imaging apparatus. The corresponding 6 cube surfaces are designated with F2a, F2b, F3a, F3b, F4a and F4b. Per definition a right-angled (x,y,z) coordinate system is associated with the magnetic coil system, the origin of which coordinate system lies in the center point of the magnetic system. The surfaces F3a and F3b lying orthogonal to the z-direction are thereby viewed as facing surfaces, contrary to which the face pairs F2a, F2b or, respectively, F4a, F4b orthogonal to the x-axis and to the y-axis are considered as lateral face pairs. The face pairs enclose a distinct three-dimensional internal or working space A. The working space A of the magnetic resonance apparatus 1 is surrounded by individual coils of the magnetic coil system.

A patient 2 to be examined lies on a patient bed of a patient positioning system in the working space A. the patient positioning system with the patient bed is not shown in FIG. 1 for clarity. A capsule-shaped endo-robot 3 is located in the hollow organ of the patient.

The (rectangular or circular) cylindrical working volume (not shown) within which magnetic forces and/or torques can be exerted on the endo-robot 3 is located symmetrically around the center point of the magnetic coil system 1 within the working space A. The longitudinal axis of the cylindrical working volume coincides with the z-axis.

The working volume exhibits, for example, a diameter of 35 cm and a length of 20 cm. In order to be able to navigate the endo-robot from the stomach up to the anus, the patient bed must be displaceable along its longitudinal axis.

For a navigation of the endo-robot 3 the magnetic resonance imaging apparatus coil system 1 comprises known means for detection of the real position of the endo-robot 4 in the working space A. Such means are, for example, the three position sensors $4_x$, $4_y$ and $4_z$ with which the position of the endo-robot 3 is determined in the respective coordinate direction. The corresponding measurement values are supplied to a regulation device 14. The magnetic resonance apparatus 1 serves as an obstacle detector that detects obstacles to the movement of the endo-robot and supplies a detector signal to the regulation device 14. Additionally, the endo-robot 3 itself may be provided with an obstacle detector 3a, which also supplies a signal to the regulation device 14 when an obstacle that impedes movement of the endo-robot through the body lumen is detected.

Figure 2:
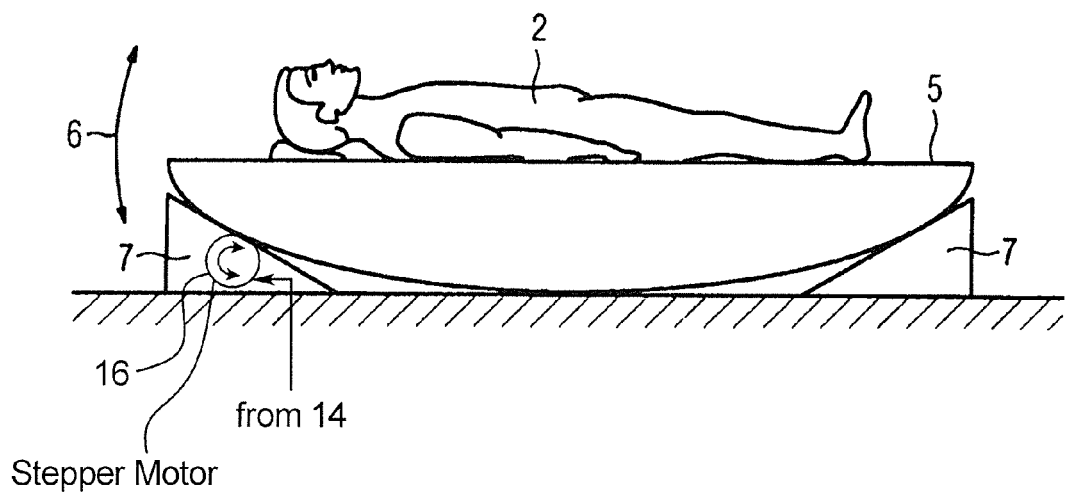
FIG. 2 is a side view of a patient bed of an embodiment of an endoscopy system.

An embodiment of a patient bed 5 that is inclined in its longitudinal axis is shown in FIG. 2. The possible inclination via which the height position of the head and feet of the patient 2 can be varied relative to the shown horizontal position is characterized by a double arrow 6, such as by the operation of a stepper motor 16 supplied with an input from the regulation device 14.

The inclination in the exemplary embodiment shown in FIG. 2 is realized via support shims 7. However, in the framework of the invention other possibilities to achieve an inclination in the longitudinal axis of the patient bed 5 are open to the average person skilled in the art.

Figure 3:
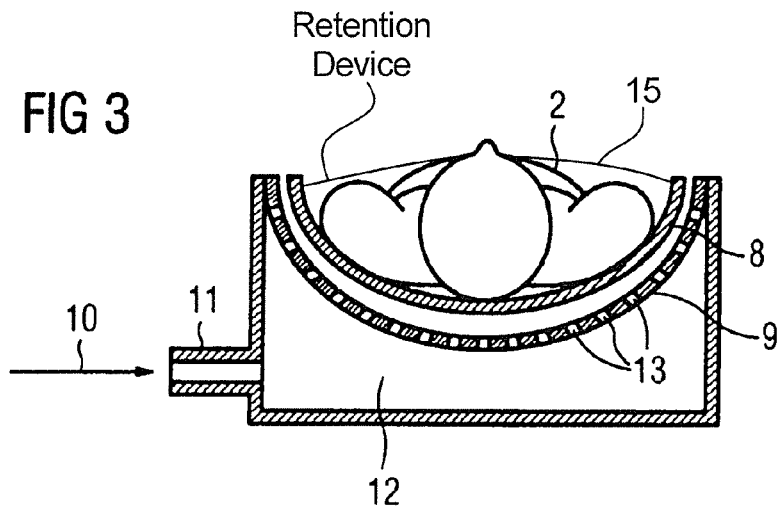
FIG. 3 is a cross-section through a patient bed of an embodiment of an endoscopy system.

In the embodiment shown in FIG. 3 a patient bed has a first supporting shell 8 that is borne in a second supporting shell afloat atop an air cushion. The supporting shell 8 that forms the actual patient bed can therewith be rotated around its longitudinal axis and thus can be correspondingly inclined.

In the shown exemplary embodiment the air cushion between the first supporting shell 8 and the second supporting shell 9 is generated in that air (arrow 10) is introduced into a chamber 12 below the second supporting shell 9 via an air feed nozzle 11. the air from the chamber 12 arrives between the two supporting shells 8 and 9 via a number of air passage openings 13 in the second bearing shell 9. The supporting shell 8 carrying the patient 2 can therewith be rotated (and therewith panned) around its longitudinal axis nearly without friction.

The measures realized in the patient bed 5 and the supporting shell 8 can also be combined with one another.

In order to avoid a position change of the patient 2, at least one patient retention device 15 is provided.

Although modifications and changes may be suggested by those skilled in the art, it is the intention of the inventors to embody within the patent warranted heron all changes and modifications as reasonably and properly come within the scope of their contribution to the art.

We claim as our invention:

1. An endoscopy system comprising:
an endo-robot configured for in vivo navigation in an anatomical lumen of a patient;
an extracorporeal magnet system that generates a temporally variable and spatially non-homogenous magnetic field that interacts with the endo-robot to move said endo-robot in said anatomical lumen;
a patient positioning system comprising a patient bed configured to receive the patient thereon while said endo-robot is in said anatomical lumen, said patient bed having a longitudinal axis and being operable to execute at least one movement, and comprising a first supporting shell, and wherein said patient bed comprises a second supporting shell with said first supporting shell being supported by an air cushion in said second supporting shell and tilting on said air cushion relative to said second supporting shell, as said at least one movement;
an obstacle detector that detects obstacles to the movement of the endo-robot in the anatomical lumen, said obstacle detector generating a detector signal upon said endo-robot encountering an obstacle to the movement of the endo-robot in the anatomical lumen; and
a control unit configured to automatically operate said extracorporeal magnetic system and said patient positioning system, and being automatically supplied with said detector signal, said control unit being configured, upon said detector signal indicating that said endo-robot has encountered an obstacle, to automatically cause said patient positioning system to execute said at least one movement to assist said endo-robot in overcoming said obstacle and to avoid said magnetic field generated by said extracorporeal magnet system from having to move the endo-robot, by virtue of the magnetic field itself, to overcome said obstacle.

2. An endoscopy system as claimed in claim 1 comprising at least one stepper motor in mechanical engagement with said patient bed, and wherein said control unit is configured to operate said stepper motor to drive said patient bed to execute said at least one movement.

3. An endoscopy system as claimed in claim 1 wherein said magnet system has a magnet system longitudinal axis and is operable to execute at least one movement selected from the group consisting of rotation around said magnitude system longitudinal axis, inclination relative to said magnet system longitudinal axis, and displacement in at least one spatial direction.

4. An endoscopy system as claimed in claim 1 wherein said obstacle detector comprises a sensor on said endo-robot that detects a counter force acting on said endo-robot in said anatomical lumen counter to said movement of said endo-robot.

5. An endoscopy system as claimed in claim 1 wherein said obstacle detector comprises an imaging system that produces, as said detector signal, an image of said obstacle.

6. An endoscopy system as claimed in claim 1 wherein said control unit is configured to derive an endo-robot position measurement from said detector signal that is indicative of a direction of movement of the endo-robot.

7. An endoscopy system as claimed in claim 1 wherein said control unit is configured to automatically control at least one of said magnet system and said patient bed to cause power consumed by said magnetic coil to be minimized or not to exceed a predetermined value.

8. An endoscopy system as claimed in claim 1 wherein said patient bed is formed substantially completely of non-ferromagnetic material.

9. An endoscopy system as claimed in claim 1 wherein said patient bed is comprised substantially completely of a material having a low electrical conductivity.

10. An endoscopy system as claimed in claim 1 wherein said patient bed comprises at least one patient retention device.

11. An endoscopy system as claimed in claim 1 comprising a closed magnetic resonance scanner and wherein said extracorporeal magnet system is a magnet system of said closed magnetic resonance scanner.

12. An endoscopy system as claimed in claim 1 comprising a closed magnetic resonance scanner and wherein said extracorporeal magnet system is a magnet system of said open magnetic resonance scanner.

* * * * *